(12) United States Patent
Tankiewicz et al.

(10) Patent No.: US 10,206,624 B2
(45) Date of Patent: Feb. 19, 2019

(54) IMPLANTATION AND ANTENNA ORIENTATION OF AN IMPLANTABLE SENSOR

(71) Applicant: Senseonics, Incorporated, Germantown, MD (US)

(72) Inventors: Szymon Tankiewicz, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 946 days.

(21) Appl. No.: 14/212,302

(22) Filed: Mar. 14, 2014

(65) Prior Publication Data
US 2014/0275859 A1    Sep. 18, 2014

Related U.S. Application Data

(60) Provisional application No. 61/798,665, filed on Mar. 15, 2013.

(51) Int. Cl.
| | |
|---|---|
| *A61B 5/00* | (2006.01) |
| *A61B 5/07* | (2006.01) |
| *A61B 5/145* | (2006.01) |
| *A61B 5/1459* | (2006.01) |
| *H04B 5/00* | (2006.01) |

(52) U.S. Cl.
CPC ............ *A61B 5/686* (2013.01); *A61B 5/0015* (2013.01); *A61B 5/0031* (2013.01); *A61B 5/076* (2013.01); *A61B 5/1459* (2013.01); *A61B 5/14532* (2013.01); *A61B 5/14546* (2013.01); *H04B 5/00* (2013.01); *H04B 5/0043* (2013.01); *H04B 5/0087* (2013.01)

(58) Field of Classification Search
CPC ..... A61B 5/0015; A61B 5/0031; A61B 5/686; H04B 5/00; H04B 5/0043; H04B 5/0087
See application file for complete search history.

(56) References Cited

U.S. PATENT DOCUMENTS

| | | | |
|---|---|---|---|
| 2004/0171355 A1* | 9/2004 | Yu .................. | A61N 1/3787 455/78 |
| 2007/0102649 A1 | 5/2007 | Colvin, Jr. et al. | |
| 2009/0298429 A1* | 12/2009 | Nakagawa .......... | H04M 1/7253 455/41.2 |

(Continued)

*Primary Examiner* — Christian Jang
*Assistant Examiner* — Karen Toth
(74) *Attorney, Agent, or Firm* — Rothwell, Figg, Ernst & Manbeck, P.C.

(57) ABSTRACT

A sensor system including an implantable sensor and an external transceiver. Aspects of the sensor system may provide improved implantation and antenna orientation of the implanted sensor. The sensor may include a sensor antenna, the transceiver may include a transceiver antenna. In some embodiments, the sensor antenna and/or transceiver antenna may include a first set of coils oriented in a first plane and a second set of coils oriented in a second plane that is different than the first plane. In some embodiments, the sensor may have a geometry that will prevent or reduce movement and/or rotation of the implanted sensor. For instance, in some embodiments, the sensor may be enclosed in silicon that contains antenna coils and/or include wings, a fluid filled sack, a swelling material, an expansion material, and/or arms.

2 Claims, 8 Drawing Sheets

(56) References Cited

U.S. PATENT DOCUMENTS

| | | | |
|---|---|---|---|
| 2010/0068996 A1* | 3/2010 | Haartsen | H04B 5/0025 |
| | | | 455/41.1 |
| 2011/0074349 A1* | 3/2011 | Ghovanloo | H02J 17/00 |
| | | | 320/108 |
| 2012/0172947 A1 | 7/2012 | Rahman et al. | |
| 2012/0322372 A1* | 12/2012 | Hansen | H04B 5/0031 |
| | | | 455/41.1 |
| 2013/0178153 A1* | 7/2013 | Thoen | H04B 5/0087 |
| | | | 455/41.1 |

* cited by examiner

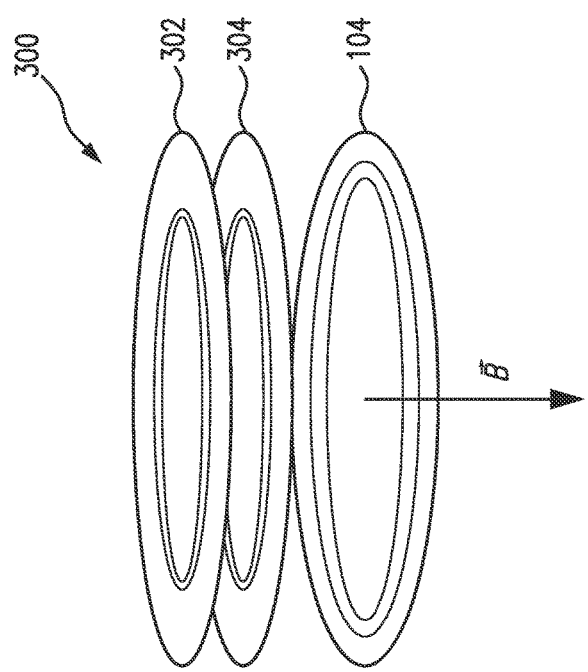

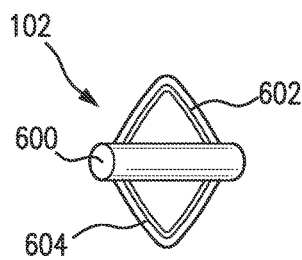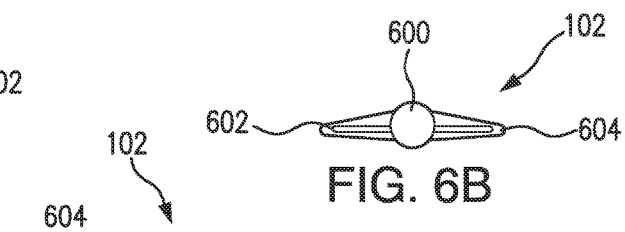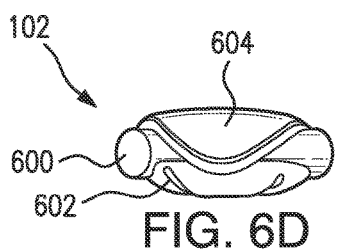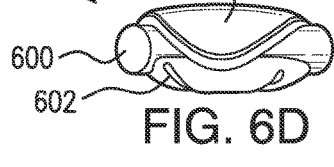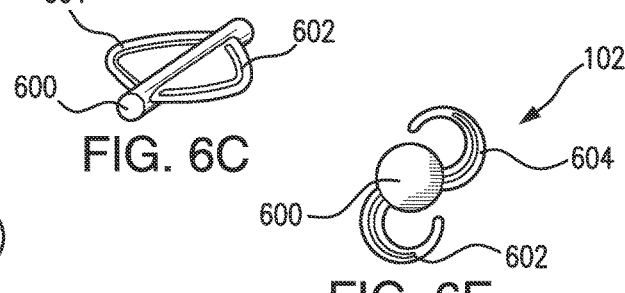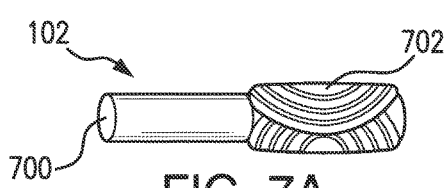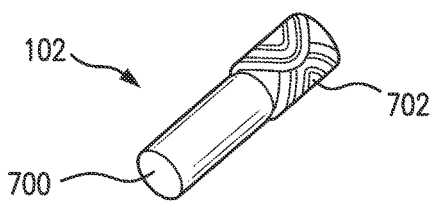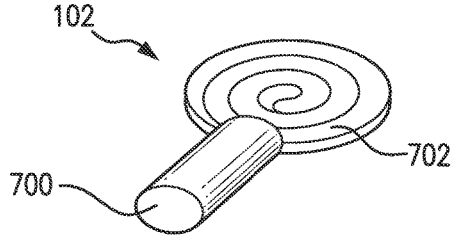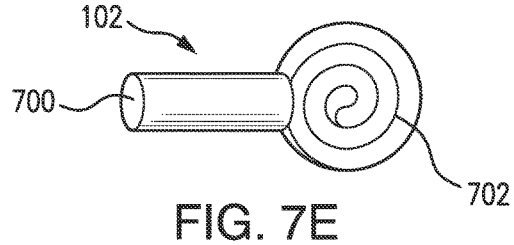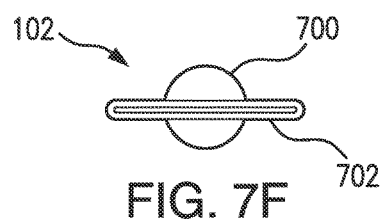

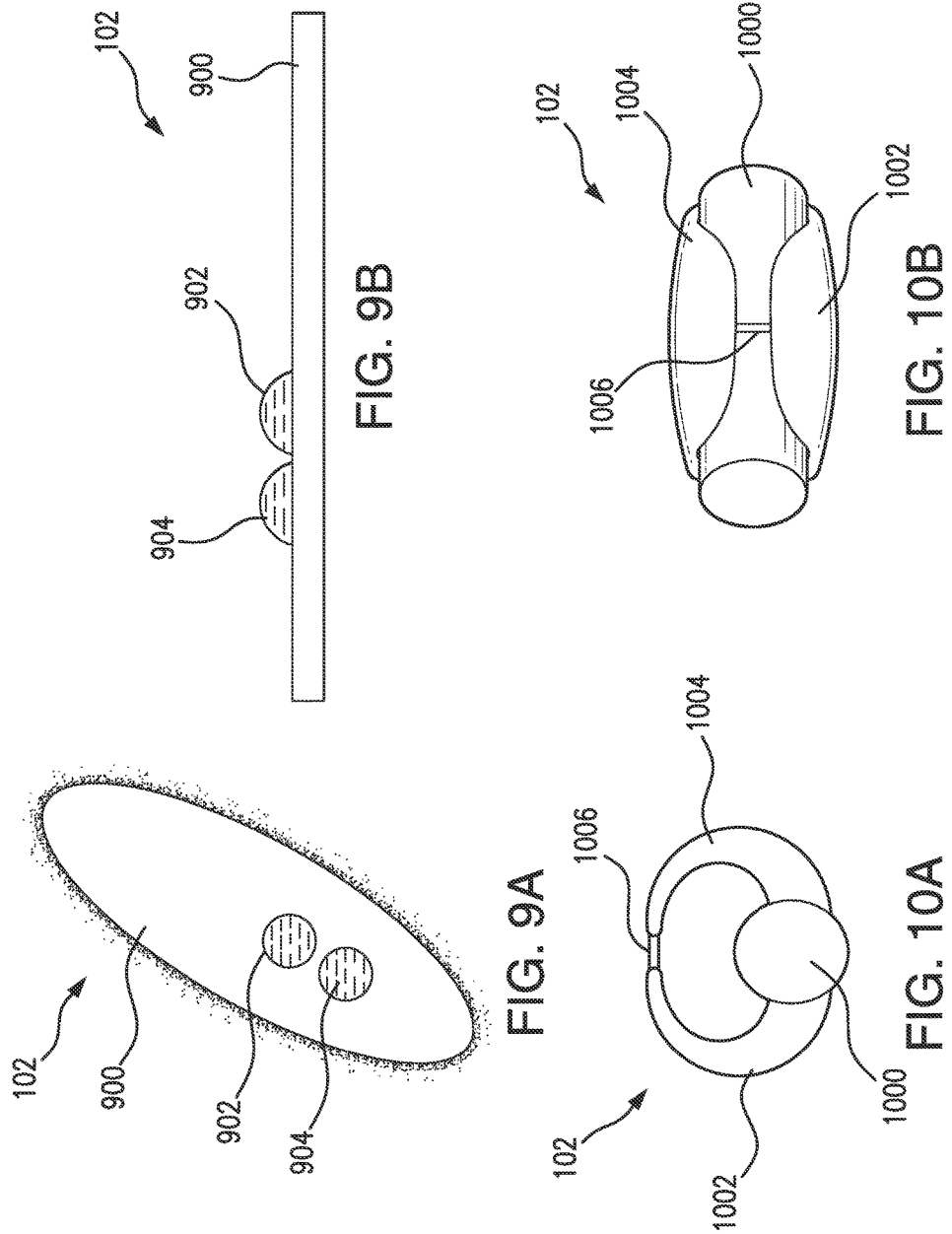

IMPLANTATION AND ANTENNA ORIENTATION OF AN IMPLANTABLE SENSOR

CROSS-REFERENCE TO RELATED APPLICATIONS

The present application claims the benefit of priority to U.S. Provisional Application Ser. No. 61/798,665, filed on Mar. 15, 2013, which is incorporated by reference in its entirety.

BACKGROUND

Field of the Invention

The present invention relates to sensor systems generally and, more specifically, to sensor systems including a sensor for implantation within a living animal for the detection of an analyte in a medium within the living animal by one or more external transceivers communicating with the sensor. The present invention also relates to improved implantation and antenna orientation of the implanted sensor.

Discussion of the Background

A sensor configured to detect an analyte, such as glucose, may be implanted in the body of a living animal, such as a human. The sensor may detect the analyte with florescent indicator molecules that emit an amount of light when irradiated with excitation light. The sensor may be passive (i.e., powered by an external source) and include an antenna to receive power from an external transceiver. An antenna present in the external transceiver may supply energy to the implanted sensor through inductive power transfer (i.e., electromagnetic transmission). The sensor rectifies the power and transfers it to an integrated circuit, which in turn activates a light source (e.g., a light emitting diode (LED)) and digitizes the appropriate response signals. The sensor then transfers the digitized response signals to the transceiver using the sensor antenna. The sensor antenna and the transceiver antenna also transfer information while inductively coupled. For example, the transceiver antenna may provide commands to the sensor, e.g., to measure an analyte, and the sensor antenna may provide analyte measurement information.

Implantable long term sensors are a recent technology and, currently, no sensor geometries and sensor antenna profiles have been developed to fixate or communicate with external transceivers. The implanted sensor may move in the body, which causes the orientation of the sensor antenna to change, as well. The sensor antenna communicates most efficiently with the transceiver antenna when antennas are parallel to each other. However, if the orientation of the sensor antennas changes due to movement of the implanted sensor, the sensor antenna and the transceiver antenna may no longer be parallel to each other. If the sensor rotates between zero and 90°, the charging by the magnetic field will be reduced. If the sensor rotates a full 90° and the sensor antenna is approximately perpendicular to the transceiver antenna, there would be no charging.

Implantable antenna size needs to be relatively large to support more efficient power and data transfer. However, clinicians and patients want a miniature device for a smaller incision and minimal pain or discomfort. In addition, the device should be flexible or elastic (conformable) to improve comfort and facilitate implantation.

Therefore, an implantable sensor is needed with an improved antenna for more efficient power and data transfer and a reduced size during implantation.

SUMMARY

The sensor system has optimal antenna performance when the implanted sensor antenna is in a parallel configuration to the transceiver antenna. The transceiver may be battery operated and the current running through the transceiver generates a magnetic field that induces a current in the sensor. The sensor may be passive and receive all of its power via the external transceiver. The external transceiver and internal sensor will have maximum efficiency in a parallel configuration due to magnetic field lines passing straight down from the transceiver to the sensor. When in this orientation, the transceiver will supply power to the sensor with the most efficiency.

One aspect of the present invention may provide two independent coils in the sensor or antenna. The first set of coils may be oriented in a first plane, and the second set of coils may be oriented in a second plane that is different than the first plane. In some embodiments, the second plane may be approximately orthogonal to the first plane. The wrapping of two independent coils may allow communication and charging if the sensor rotates. In some embodiments, a transceiver having two or more antennas may use only one coil at a time, and, ideally, the looped wire of the coil will be parallel to the antenna allowing for maximum absorption of the magnetic field. If the sensor rotates $0° < \varphi < 90°$, the charging by the magnetic field will be reduced in sensors with only one set of coils. However, in a system with 1-N antennas, the transceiver may activate antenna 1, antenna 2, antenna N, and the transceiver may choose the antenna that is coupling or receiving maximum power returning maximum signal when sending back data. In some embodiments, the transceiver may use multiple antennas if a combination of antennas yields more power.

The multilayer antenna design concept may apply to the implantable sensor, as well. The sensor may be small so that the incision used to implant the sensor in the patient may also be small, thus reducing the likelihood of discomfort. The sensor's design requirements may not allow much room for an antenna coil. Because there may be a minimal amount of space for the coil, the coils may be stacked in order to provide sufficient power generation.

Another aspect of the present invention may provide a set of coils in silicon outside the sensor. The silicon may be a small, flat, round or oblong shape that encloses the sensor and may contain antenna coils. This shape may limit the sensor's ability to rotate while optimizing the antenna size and orientation relative to the transceiver. Silicone can be compressed, rolled up, etc. allowing the sensor to be inserted through a small incision ("key hole") before being expanded, unrolled, etc. to deploy the antenna.

Another aspect of the present invention may provide a titanium nickel framed sensor to allow for different shaped sensor configurations. For example, the sensor may include wings that can uncurl after insertion to increase the surface area of the sensor. TiNi is a memory alloy that, when attached to the sensor, will uncurl to increase the surface area of the sensor. The larger surface area decreases the sensor's ability to move or rotate.

Another aspect of the present invention may provide a fluid filled sack attached to the sensor to expand and enlarge the sack. A fluid configured to respond to temperature increases may be used and, when the fluid is warmed to body temperature, it expands and enlarges the sack, which immobilizes the sensor. The fluid may be, for example, a liquid such as 1,1,1,4,4,4 hexafluorobutane.

Another aspect of the present invention may provide a material in the sensor that swells a great deal when wet. For example, a material such as acrylic acid may be used. Fluid may enter the sensor through osmotic pressure to allow the material in the sensor to become wet.

Another aspect of the present invention may provide materials that expand when mixed together. The materials may be mounted in or on the sensor, and, when introduced to a disturbance (e.g., mechanical compression), the separate fluids may be allowed to interact. The combined fluids may cause swelling in the surrounding material.

Another aspect of the present invention may provide the sensor with arms that are folded or rolled up and joined to each other by a seal. When the seal is destroyed, the arms extend outwardly and immobilize the sensor. In one embodiment, the seal may be broken by applying a lithtripsy burst (e.g., ultrasound). In another embodiment, the seal may be a resistive material and application of a high current dissolves the seal (e.g., neurovascular coils). In another embodiment, the seal may be made of an element that dissolves in water (e.g., zinc). A protective coating may be used to prevent moisture from opening the arms, and this coating would be removed after implantation or may also dissolve in water.

In aspects of the invention in which a chemical expands to immobilize the sensor, the sensor and arm areas can be punctured, cooled or injected with a substance that reverses the chemical reaction when the sensor needs to removed.

By allowing different geometries of the sensor and/or the antenna there will be a reduced tendency for the sensor to lose communication with outside tools (e.g., portable scanning device/transceiver). The changes in sensor geometry will increase the sensor's ability to stay locally fixated and reduce the tendency to rotate or twist within the patient.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 3 illustrates an exploded view of a multiple coil antenna for a transceiver embodying aspects of the present invention.

FIGS. 6A-6E illustrate top views, front views and perspective views of a sensor with a memory metal frame embodying aspects of the present invention.

FIGS. 7A-7F illustrate top views, rear views and perspective views of a sensor with a memory metal frame embodying aspects of the present invention.

FIGS. 9A-9B illustrate a top view and a perspective view of a sensor having two materials configured to expand when mixed together embodying aspects of the present invention.

FIGS. 10A-10B illustrate a front view and a perspective view of a sensor having arms coupled together by a removable seal embodying aspects of the present invention.

DETAILED DESCRIPTION OF PREFERRED EMBODIMENTS

Figure 1:
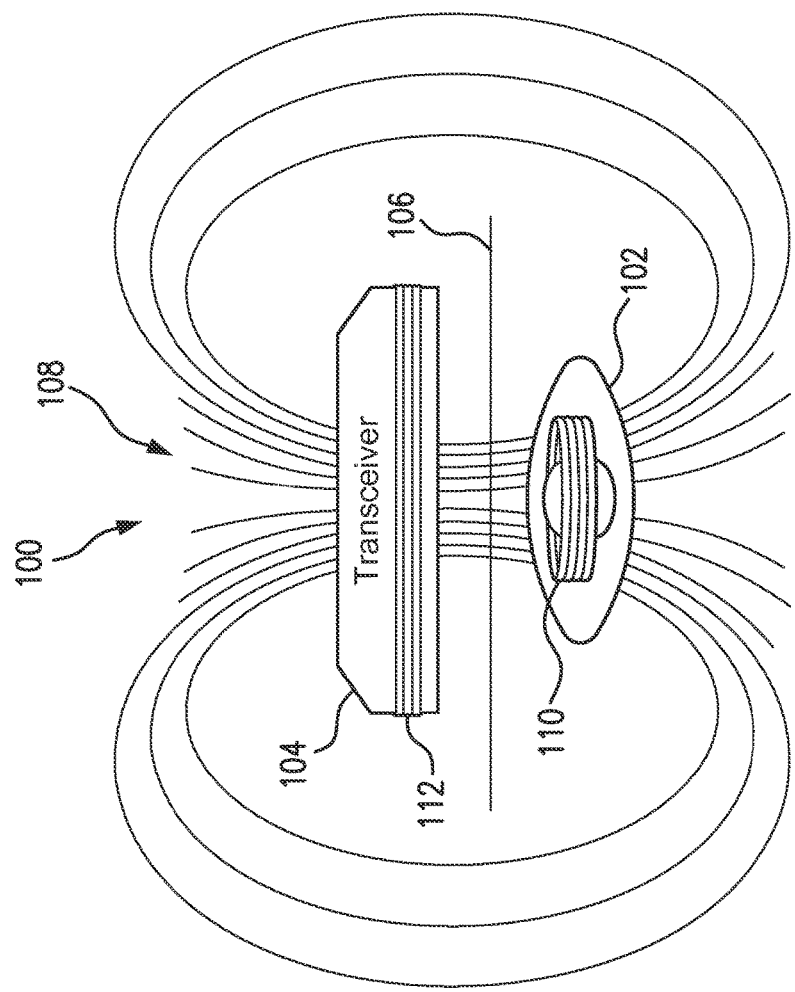
FIG. 1 illustrates a schematic view of a sensor system, which includes an implanted sensor and a transceiver, known in the art.

FIG. 1 illustrates a schematic view of a sensor system, which includes an implanted sensor and a transceiver, known in the art. The sensor system 100 includes an implantable sensor 102 and a transceiver 104. The sensor 102 is implanted under the skin 106 (i.e., in the subcutaneous or peritoneal tissues) of a mammal, such as a human, and is configured to detect an analyte. The sensor 102 may detect the analyte with florescent indicator molecules that emit an amount of light when irradiated with excitation light provided by a light source. The sensor 102 and the transceiver 104 each include at least one antenna 110, 112, such as a coil, and the sensor 102 receives power from and communicates with the transceiver 104 through the antennas 110, 112. The transceiver 104 generates a magnetic field 108 that induces a current in the sensor 102, which provides power and manipulation of the magnetic field can communicate information between the transceiver 104 and sensor 102. The transmission of power and information between the transceiver 104 and the sensor 102 is most efficient when the antennas are parallel to each other and the magnetic field 108 passes straight down from the transceiver 104 to the sensor 102. However, in the previous sensor systems, the orientation of the sensor 102 and its antenna 110 in the body may change after implantation and positioning the antenna 112 of the transceiver 104 parallel to the antenna 110 of the sensor 102 can be difficult.

Figure 2A:
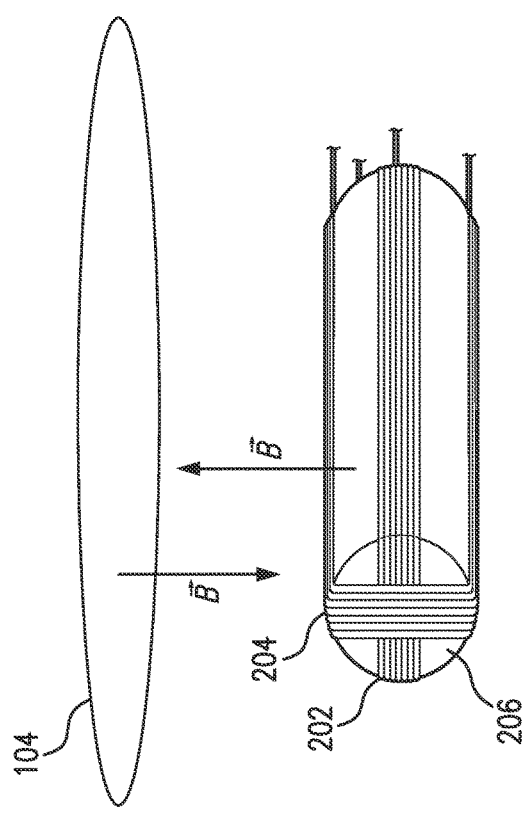
FIGS. 2A-2C illustrate a top view, a front view and a perspective view, respectively, of a multiple coil antenna embodying aspects of the present invention.
Figure 2B:
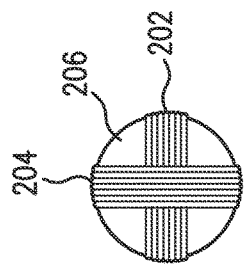
Figure 2C:
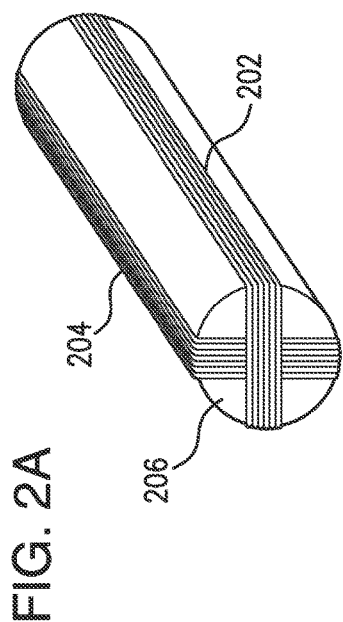

FIGS. 2A-C and 3 illustrate a multiple coil antenna embodying aspects of the present invention. The multiple coil antenna 200 includes a first set of coils 202 and a second set of coils 204 on a body 206. The first set of coils 202 is oriented in a first plane and the second set of coils 204 is oriented in a second plane that is different than the first plane. In an embodiment of the present invention, the second plane is approximately orthogonal to the first plane. The multiple coil antenna 200 may be used in the sensor 102 and/or the transceiver 104. FIG. 2A illustrates a multiple coil antenna 200 in a sensor 102 and communicating with a transceiver 104. The sensor's design requirements may not allow much room for an antenna 200, and, because there may be a minimal amount of space for the antenna 200, the sets of coils may be stacked in order to generate sufficient power. The wrapping of two independent sets of coils 202 and 204 in the sensor 102 may allow the transceiver 104 to efficiently communicate and power the sensor 102 if the sensor 102 rotates.

Figure 2D:
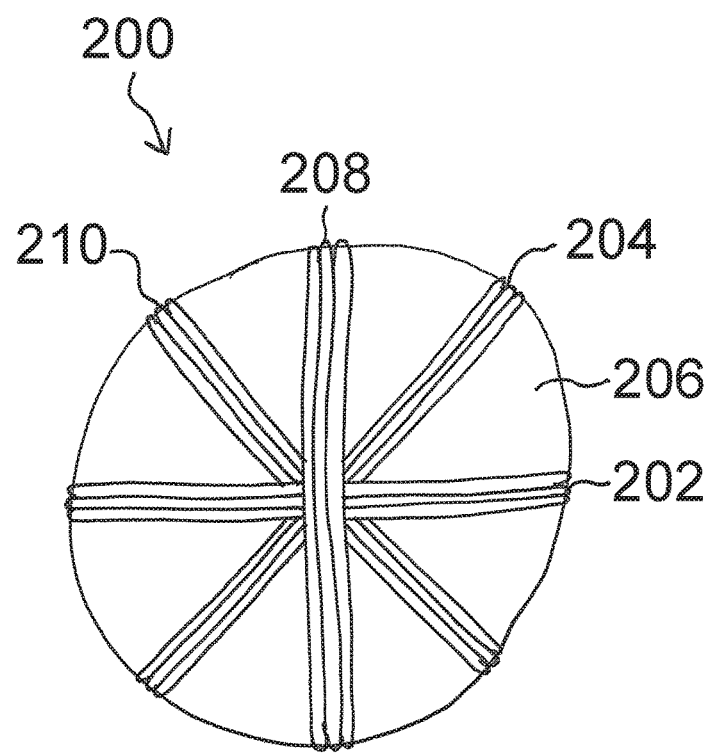
FIG. 2D illustrates front view of a multiple coil antenna embodying aspects of the present invention.

In an embodiment of the present invention, only one set of coils is used at a time, and a controller of the transceiver 104 or sensor 102 may determine which set of coils is most efficiently communicating with the transceiver 104 or sensor 102. In an embodiment of the present invention, the multiple coil antenna 200 can include any number of antennas, and in a system with 1-N sets of coils, the sensor 102 or transceiver 104 can activate any of coil 1, coil 2, and coil N. For example, as shown in FIG. 2D, if the multiple coil antenna 200 includes four sets of coils, the antenna 200 may include a first coil 202 in a first plane, a second coil 204 in a second plane approximately 45° relative to the first plane, a third coil 208 in a third plane approximately orthogonal to the first plane and approximately 45° to the second plane, and a fourth coil 210 in a fourth plane approximately orthogonal to the second plane and approximately 45° to the third plane. In an embodiment of the present invention, multiple set of coils may be combined (i.e., activated at the same time) if a combination yields more power.

Figure 4A:
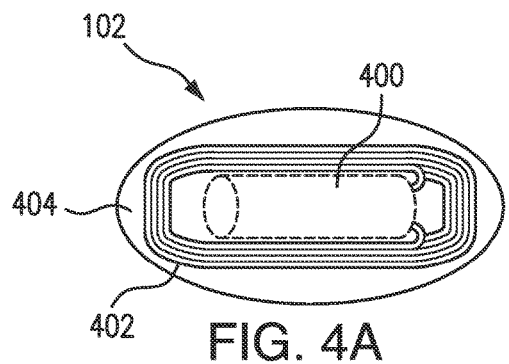
FIGS. 4A-4C illustrate a top view, a front view and a perspective view, respectively, of a sensor with an antenna outside the main body embodying aspects of the present invention.
Figure 4B:
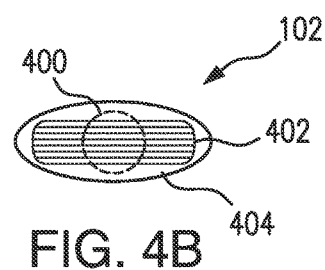
Figure 4C:
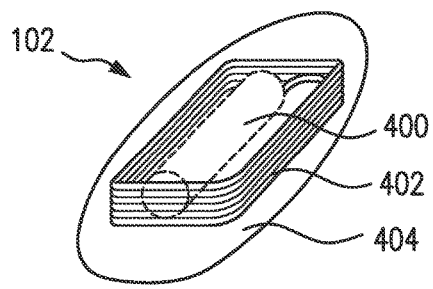
Figure 5A:
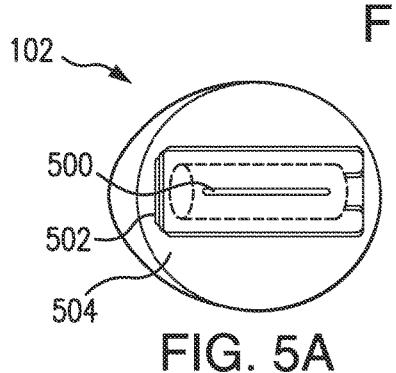
FIGS. 5A-5C illustrate a top view, a front view and a perspective view, respectively, of a sensor with an antenna outside the main body embodying aspects of the present invention.
Figure 5B:
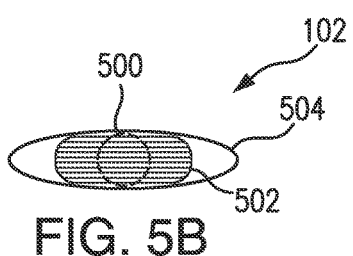
Figure 5C:
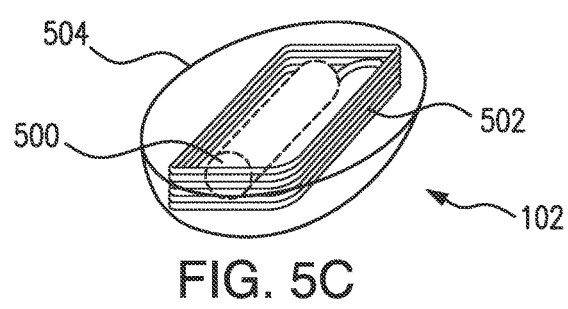
Figure 8A:
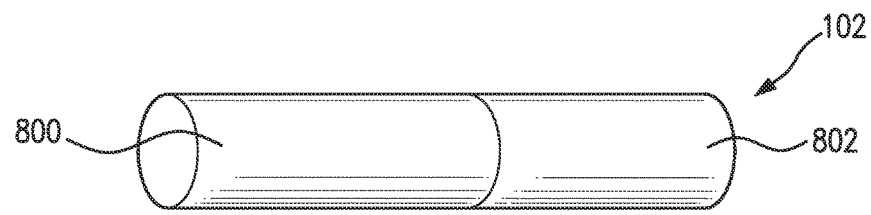
FIGS. 8A-8D illustrate top views and perspective views of a sensor with fluid filled sack embodying aspects of the present invention.
Figure 8B:
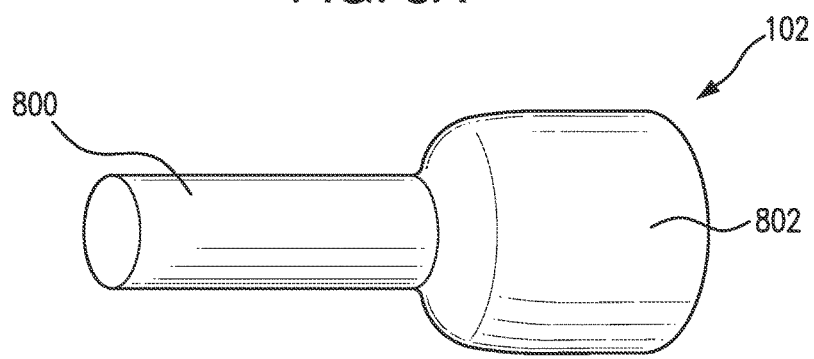
Figure 8C:
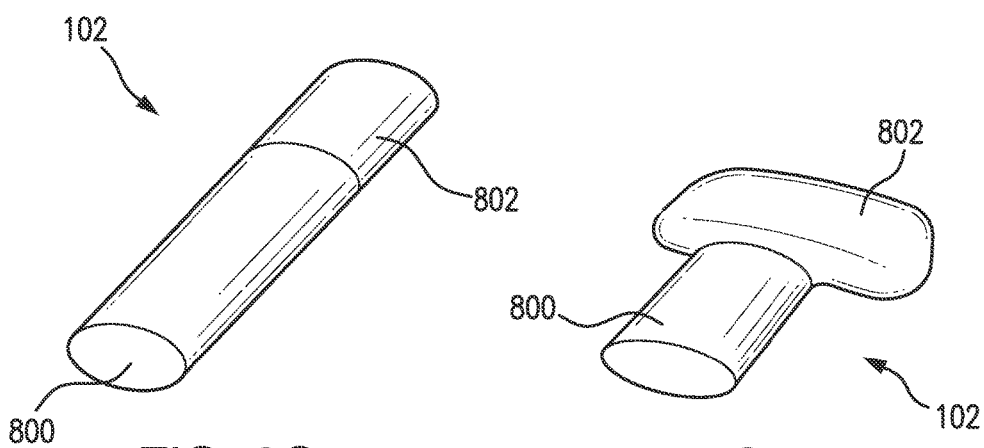
Figure 8D:
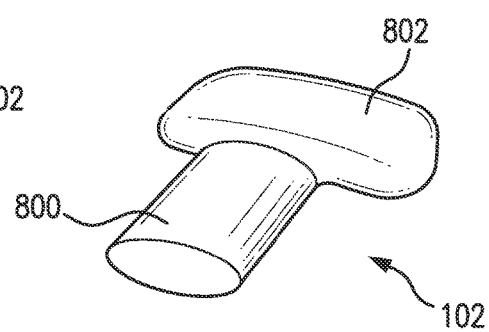

FIGS. 4A-C and 5A-C illustrate a sensor with an antenna outside the main body embodying aspects of the present invention. As illustrated in FIGS. 4A-C, the sensor 102 may include a main body 400, an antenna 402 outside the main body 400 of the sensor 102, and a casing 404 surrounding the main body 400 and the antenna 402. In some embodiments, the casing 404 may have an oblong shape that encloses the sensor body 400 and the antenna coils 402. As illustrated in FIGS. 5A-C, the sensor 102 may include a main body 500, an antenna 502 outside the main body 500 of the sensor 102, and a casing 504 surrounding the main body 500 and the antenna 502. In some embodiments, the casing 504 may have a small, flat, round shape that encloses the sensor body 500 and the antenna coils 502. In some embodiments, the main body 400 (or 500) may include the components for the sensor except for the antenna, such as, for example, a light source, a photodiode and indicator molecules. Placing the antenna 402 (or 502) outside of the main body 400 (or 500) allows for the antenna 402 (or 502) to have a larger cross sectional area (i.e., the area in a plane transverse to a longitudinal axis of the coils and enclosed within the coils), which may be advantageous because the larger the cross sectional area of the antenna 402 (or 502) the more efficiently it transmits data and power. In an embodiment of the present invention, the casing 404 (or 504) may be a polymer such as silicone or any other suitable soft polymer. The shape of the casing 404 (or 504) may limit the ability of the sensor 102 to rotate after implantation while optimizing the antenna size and orientation relative to the transceiver. In some embodiments, the casing 404 (or 504) can be compressed, rolled up, etc. allowing the sensor 102 to be inserted through a small incision ("key hole") before being expanded and deployed.

FIGS. 6A-E and 7A-F illustrate a sensor with a memory metal frame embodying aspects of the present invention. As illustrated in FIGS. 6A-E, the sensor 102 may include a body 600 and an expandable frame 602, 604. As illustrated in FIGS. 7A-F, the sensor 102 may include a body 700 and an expandable frame 702. In one non-limiting embodiment, the expendable frame 602, 604 and 702 may be composed of titanium nickel memory metal or other material having similar properties. The expandable frame may comprise wings 602 and 604, a thin end portion 702, or any other sensor shape configuration. The wings 602 and 604 are curled around the sensor body 600 during insertion of the sensor 102 into the patient. After the sensor 102 has been inserted into the patient, the wings 602 and 604 are uncurled to increase the surface area of the sensor 102 and prevent the sensor 102 from moving or rotating within the patient. In an embodiment of the present invention, the wings 602 and 604 may be mechanically uncurled or unfolded by a surgeon after insertion of the sensor 102. The thin end portion 702 may be curled during implantation (e.g., such that its width does not exceed the width of the sensor body 700). In an embodiment of the present invention, the sensor body 700 is cylindrical, and the diameter of the curled end portion 702 does exceed the diameter of the circular cross section of the sensor body 700. After the sensor 102 has been inserted into the patient, the end portion 702 may be uncurled into a flat, circular shape that increases the surface area of the sensor 102 and limits or prevents movement and/or rotation of the sensor 102 within the patient. The end portion 702 may be mechanically uncurled or unfolded by the surgeon after implantation of the sensor 102. The end portion 702 may be uncurled into any shape that increases the surface area of the sensor, e.g., a square, a rectangle or an oval. Thus, the size of the sensor can be minimized for implantation and then expanded to an operational size after implantation.

FIGS. 8A-D illustrate top views and perspective views of a sensor with fluid filled sack embodying aspects of the present invention. The sensor 102 includes a main body 800 and an expandable sack 802 coupled to the main body 800. The sack 802 may be filled with a fluid that can be expanded after implantation. For example, a substance may be a liquid outside of the body at room temperature and a gas inside the body of the patient when the substance is warmed to body temperature. In an embodiment of the present invention, the substance may be, for example, 1,1,1,4,4,4 hexafluorobutane. When the substance becomes a gas, it expands and causes the sack 802 to enlarge and cover more surface area, which prevents the sensor 102 from moving or rotating. In another embodiment of the present invention, the substance in the sack 802 may be a material that swells a great deal when wet. For example, a substance such as acrylic acid may be used. Liquid may enter the sack 802 through osmotic pressure to allow the substance in the sack 802 to become wet and swell.

FIGS. 9A-B illustrate a top view and a perspective view of a sensor inside an encapsulation comprised of two materials configured to expand when mixed together. The sensor 102 may include a casing 900 and two materials 902 and 904 on the casing 900 that cause the casing 900 to swell when mixed together. The sensor is inside the casing 900. The materials 902 and 904 may be mounted in or on the casing 900, and, may be allowed to interact when subject to a disturbance (e.g., mechanical compression) to dissolve, burst or otherwise alter a seal or other barrier separating materials 902 and 904. The combined materials 902 and 904 may cause swelling in the casing 900, which may prevent or limit movement and/or rotation of the sensor 102.

FIGS. 10A-B illustrate a front view and a perspective view of a sensor having arms coupled together by a removable seal embodying aspects of the present invention. In one embodiment, the sensor 102 may include a main body 1000, two arms 1002 and 1004 coupled to the main body 1002 at a first end of each arm, and a seal 1006 coupling the arms 1002 and 1004 to each other at a second end. When the seal 1006 is present, the arms 1002 and 1004 are joined to give the sensor 102 an approximately circular cross section, which helps to reduce the height and width of the sensor 102 during implantation. After implantation, the seal 1006 is altered to release arms 1002 and 1004, and the arms 1002 and 1004 extend outwardly, which immobilizes the sensor 102. In one non-limiting embodiment, the seal 1006 may be broken by applying a lithtripsy burst (e.g., ultrasound). In another embodiment, the seal 1006 may be a resistive material, and application of a high current may dissolve the seal 1006 (e.g., neurovascular coils). In another embodiment, the seal 1006 may be made of an element that dissolves in water (e.g. zinc). A protective coating may be used to prevent moisture from destroying the seal 1006 and prematurely releasing the arms 1002 and 1004. The coating would be removed after implantation or may also dissolve in water, but at a slower rate than the material of which the seal 1006 is composed.

Embodiments of the present invention have been fully described above with reference to the drawing figures. Although the invention has been described based upon these preferred embodiments, it would be apparent to those skilled in the art that certain modifications, variations and alternative constructions could be made to the described embodiments within the spirit and scope of the invention. For example, any of the wings for a sensor discussed above may be configured to swell after being uncurled by, for example, including materials that swell when combined together. Further, in embodiments in which the sensor includes wings to immobilize it, the sensor may include more than two wings. For example, the sensor may include four wings that are each approximately orthogonal to the adjacent wings.

We claim:

1. A sensor system, comprising:
a sensor including a sensor antenna; and
a transceiver including a transceiver antenna including first coils, second coils, third coils, and fourth coils,
wherein the first, second, third, and fourth coils of the transceiver antenna are configured to couple with the sensor antenna, the first coils are oriented in a first plane, the second coils are oriented in a second plane at a first non-zero angle relative to the first plane, the third coils are oriented in a third plane at the first non-zero angle relative to the second plane, the third plane is at a second non-zero angle relative to the first plane, the fourth coils are oriented in a fourth plane at the first non-zero angle relative to the third plane, the fourth plane is at the second non-zero angle relative to the second plane, and the first non-zero angle and the second non-zero angle are different non-zero angles;
wherein the first non-zero angle is approximately 45 degrees, and the second non-zero angle is approximately 90 degrees.

2. A sensor system, comprising:
a sensor including a sensor antenna having first coils, second coils, third coils, and fourth coils; and
a transceiver including a transceiver antenna,
wherein the first, second, third, and fourth coils of the sensor antenna are configured to couple with the transceiver antenna, the first coils are oriented in a first plane, the second coils are oriented in a second plane different than the first plane, the third coils that are oriented in a third plane different than the first and second planes, the second plane is at a first non-zero angle relative to the first plane, the third plane is at the first non-zero angle relative to the second plane, the third plane is at a second non-zero angle relative to the first plane, fourth coils that are oriented in a fourth plane different than the first, second, and third planes, the fourth plane is at the first non-zero angle relative to the third plane, the fourth plane is at the second non-zero angle relative to the second plane, and the first non-zero angle and the second non-zero angle are different non-zero angles;
wherein the first non-zero angle is approximately 45 degrees, and the second non-zero angle is approximately 90 degrees.

* * * * *